US009441430B2

(12) United States Patent
Selman et al.

(10) Patent No.: US 9,441,430 B2
(45) Date of Patent: Sep. 13, 2016

(54) DRILLING RIG WITH CONTINUOUS GAS ANALYSIS

(71) Applicant: SELMAN AND ASSOCIATES, LTD., Midland, TX (US)

(72) Inventors: Thomas H. Selman, Midland, TX (US); Matthew J. Jennings, Midland, TX (US); Stephen M. Bergman, Casper, WY (US)

(73) Assignee: SELMAN AND ASSOCIATES, LTD., Midland, TX (US)

(*) Notice: Subject to any disclaimer, the term of this patent is extended or adjusted under 35 U.S.C. 154(b) by 715 days.

(21) Appl. No.: 13/863,996

(22) Filed: Apr. 16, 2013

(65) Prior Publication Data

US 2013/0270006 A1 Oct. 17, 2013

Related U.S. Application Data

(60) Provisional application No. 61/625,371, filed on Apr. 17, 2012.

(51) Int. Cl.
*E21B 21/06* (2006.01)
*E21B 49/00* (2006.01)
*E21B 49/08* (2006.01)
*G01N 33/00* (2006.01)

(52) U.S. Cl.
CPC ............ *E21B 21/067* (2013.01); *E21B 49/005* (2013.01); *E21B 49/08* (2013.01); *E21B 49/084* (2013.01); *G01N 33/0006* (2013.01)

(58) Field of Classification Search
CPC .... E21B 49/08; E21B 49/005; E21B 49/084; E21B 49/085; E21B 21/01; E21B 21/067; E21B 2049/085; G01N 33/0004; G01N 33/0006

USPC .............. 73/152.46, 152.23, 152.02, 152.17, 73/152.28, 19.09; 702/6, 9, 11, 12; 166/264, 265, 267; 175/206, 207, 24, 175/38, 40, 42

See application file for complete search history.

(56) References Cited

U.S. PATENT DOCUMENTS

| 2,752,777 | A | | 10/1950 | Jacobs et al. |
| 2,752,776 | A | | 4/1954 | Kapff et al. |
| 2,704,658 | A | * | 3/1955 | Gordon ..................... B01F 7/22 175/206 |
| 3,118,299 | A | * | 1/1964 | Worthington ........ G01N 33/241 436/141 |
| 3,616,599 | A | * | 11/1971 | Burnham, Sr. .... B01D 19/0021 137/533.11 |
| 4,088,457 | A | * | 5/1978 | Phillips .............. B01D 19/0047 96/196 |

(Continued)

*Primary Examiner* — Michael A Lyons
*Assistant Examiner* — David L Singer
(74) *Attorney, Agent, or Firm* — Buskop Law Group, PC; Wendy Buskop

(57) ABSTRACT

A drilling rig having continuous gas analysis can include a substructure, base, mast, pipe handler, mud pump, drilling rig power source, drawworks, cabling, rotating head, blowout preventer, drill string, and drill bit. A rig server of the drilling rig can have a rig processor and rig data storage for implementing rig operations. Piping can be in fluid communication between the blowout preventer and a gas analyzer system for real-time measurement of a concentration of gases in a drilling fluid. The gas analyzer system can include a sample chamber, means for agitating and creating a vortex, gas capturing chamber for receiving liberated fluid, gas analyzer for providing real-time gas speciation of the liberated fluid, suction pump for pulling the liberated fluid, filtration means, exhaust port, and exhaust line for flowing non-analyzed fluid to a drilling fluid storage chamber, drilling fluid conduit, or both.

26 Claims, 12 Drawing Sheets

(56) References Cited

U.S. PATENT DOCUMENTS

| | | | |
|---|---|---|---|
| 4,272,258 A | 6/1981 | Shifflett | |
| 4,358,295 A | 11/1982 | Ratcliff | |
| 4,358,298 A * | 11/1982 | Ratcliff | E21B 21/067 366/137 |
| 4,393,304 A * | 7/1983 | Ishida | G01N 21/3518 250/343 |
| 4,414,651 A | 11/1983 | Buckner | |
| 4,447,247 A * | 5/1984 | Naess | E21B 43/0122 210/170.11 |
| 4,565,086 A | 1/1986 | Orr, Jr. | |
| 4,616,321 A | 10/1986 | Chan | |
| 4,635,735 A * | 1/1987 | Crownover | E21B 49/08 175/42 |
| 4,670,139 A | 6/1987 | Spruiell et al. | |
| 4,831,559 A | 5/1989 | Miller | |
| 4,887,464 A * | 12/1989 | Tannenbaum | E21B 49/005 175/206 |
| 5,058,674 A | 10/1991 | Schultz et al. | |
| 5,199,509 A | 4/1993 | Wright et al. | |
| 5,237,539 A | 8/1993 | Selman | |
| 5,329,811 A | 7/1994 | Schultz et al. | |
| 5,648,603 A | 7/1997 | Hanson | |
| 5,869,343 A | 2/1999 | Handschuck et al. | |
| 6,073,709 A | 6/2000 | Hensley | |
| 6,496,309 B1 | 12/2002 | Bilton et al. | |
| 6,505,523 B1 | 1/2003 | Taylor et al. | |
| 6,546,818 B2 | 4/2003 | Taylor et al. | |
| 6,609,433 B2 | 8/2003 | Taylor et al. | |
| 6,666,099 B2 | 12/2003 | Taylor | |
| 6,873,267 B1 * | 3/2005 | Tubel | E21B 43/12 166/250.15 |
| 6,993,979 B2 * | 2/2006 | Segeral | G01F 1/44 73/861.64 |
| 7,099,003 B2 | 8/2006 | Saptari et al. | |
| 7,219,541 B2 | 5/2007 | DiFoggio et al. | |
| 7,844,400 B1 | 11/2010 | Selman et al. | |
| 7,957,903 B1 | 6/2011 | Selman et al. | |
| 8,132,452 B1 | 3/2012 | Selman et al. | |
| 8,204,717 B2 | 6/2012 | McLaughlin et al. | |
| 2003/0105535 A1 * | 6/2003 | Rammler | G05B 19/409 700/17 |
| 2005/0247599 A1 * | 11/2005 | Browne | C10G 27/04 208/3 |
| 2006/0202122 A1 * | 9/2006 | Gunn | G01N 21/3504 250/339.13 |
| 2006/0254421 A1 * | 11/2006 | Boone | E21B 21/067 95/260 |
| 2007/0050154 A1 | 3/2007 | Albahri | |
| 2009/0077936 A1 * | 3/2009 | Sterner | E21B 49/005 55/422 |
| 2010/0027004 A1 | 2/2010 | Bonyuet et al. | |
| 2010/0089120 A1 | 4/2010 | Hanson | |
| 2010/0175467 A1 | 7/2010 | DiFoggio et al. | |
| 2011/0280104 A1 * | 11/2011 | McClung, III | E21B 3/02 367/82 |
| 2011/0308391 A1 | 12/2011 | DeGreeve et al. | |
| 2012/0000278 A1 * | 1/2012 | Phillips | B01D 19/0052 73/152.04 |
| 2012/0234599 A1 * | 9/2012 | Brumboiu | E21B 21/01 175/50 |
| 2013/0085674 A1 * | 4/2013 | Zhdaneev | E21B 49/10 702/6 |
| 2013/0106586 A1 * | 5/2013 | Vidal | G05B 15/02 340/12.22 |
| 2013/0192360 A1 * | 8/2013 | Jamison | E21B 21/00 73/152.19 |
| 2014/0260993 A1 * | 9/2014 | Elms | E21B 21/067 96/397 |

* cited by examiner

DRILLING RIG WITH CONTINUOUS GAS ANALYSIS

CROSS REFERENCE TO RELATED APPLICATION

The present application claims priority to and the benefit of U.S. Provisional Patent Application Ser. No. 61/625,371 filed on Apr. 17, 2012, entitled "DRILLING RIGHT WITH CONTINUOUS GAS ANALYSIS." This reference is hereby incorporated in its entirety.

FIELD

The present embodiments generally relate to a drilling rig with continuous gas analysis.

BACKGROUND

A need exists for a drilling rig with continuous gas analysis for use with natural gas wells, oil wells, and other wells that can potentially emit at least some gases or vapors.

A need exists for a drilling rig with continuous gas analysis that can analyze high pressure fluid streams, while simultaneously providing for a quick and accurate analysis of a homogenous mixture of a drilling fluid conduit.

A need exists for a drilling rig with continuous gas analysis that enables workers proximate to a drilling site to be immediately aware of a presence of combustible gases, such as hydrogen gas; thereby allowing the workers to take precautionary measures to prevent explosions or loss of life.

A need exists for a drilling rig with continuous gas analysis for sampling gases and vapors via a modular gas capturing component that is easy to manufacture, repair, and install in the field.

A need exists for a drilling rig with continuous gas analysis with a gas capturing component that is strong, able to stand up independently, and able to withstand physical impacts in the field.

A need exists for a drilling rig with continuous gas analysis that can be remotely monitored and controlled, such as in areas with terrorist activity; thereby reducing a potential for harm to workers.

The present embodiments meet these needs.

BRIEF DESCRIPTION OF THE DRAWINGS

The detailed description will be better understood in conjunction with the accompanying drawings as follows.

Figure 1:
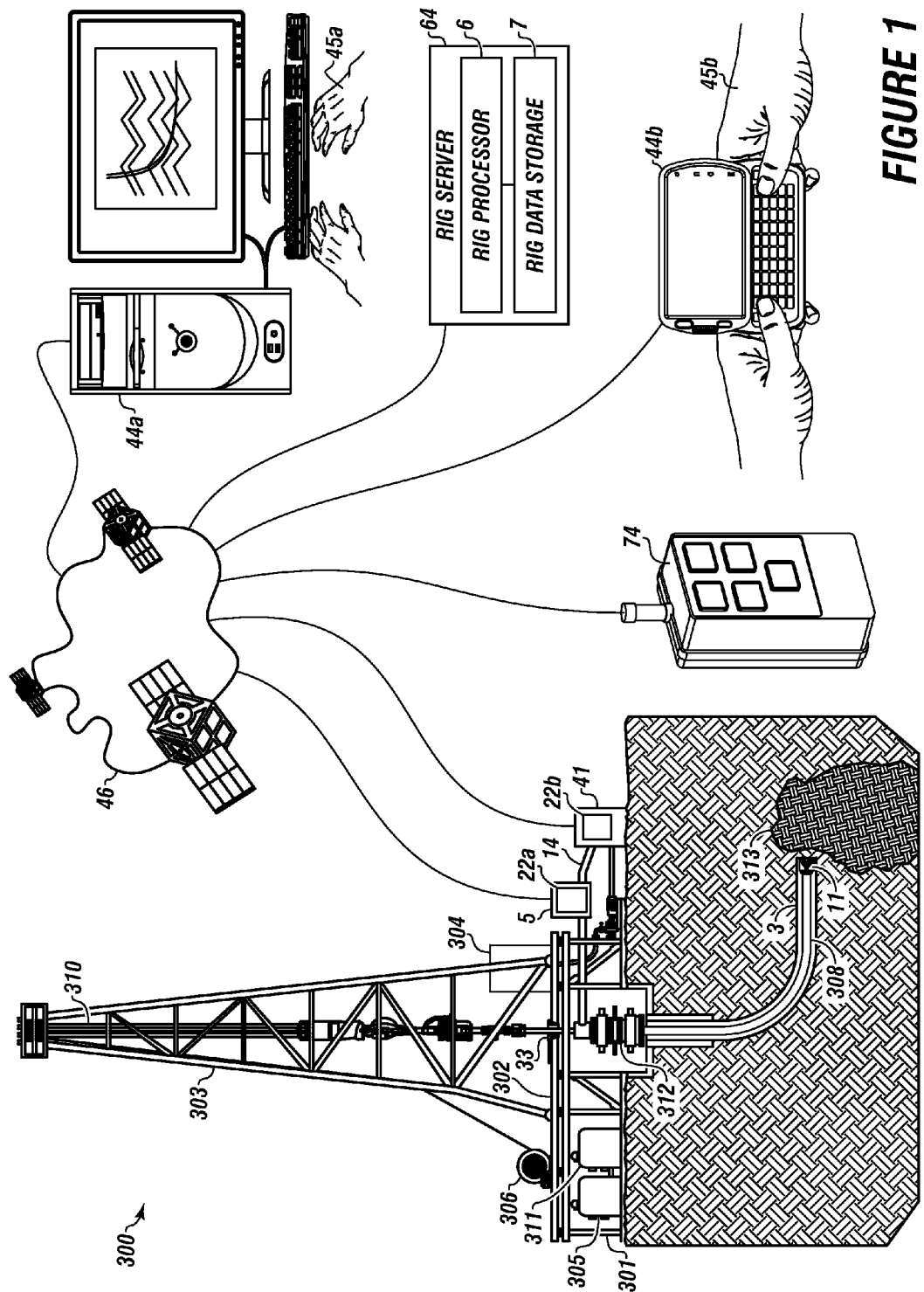
FIG. 1 depicts the drilling rig having continuous gas analysis according to one or more embodiments.

The present embodiments are detailed below with reference to the listed Figures.

DETAILED DESCRIPTION OF THE EMBODIMENTS

Before explaining the present system in detail, it is to be understood that the system is not limited to the particular embodiments and that it can be practiced or carried out in various ways.

The present embodiments relate to a drilling rig having continuous gas analysis.

The drilling rig can be a land based rig, semisubmersible rig, portable rig with self-propulsion, skid mounted rig, jack-up rig, tension leg platform rig, drilling ship rig, deep draft cassion vessel rig, rotary drilling rig, single or simultaneously dual lifting drilling rig, or the like.

In one or more embodiments, the drilling rig can be configured for pneumatic drilling, foam drilling, oil based mud drilling, water based mud drilling, hydraulic drilling, or the like.

The drilling rig can have a drill bit for drilling a wellbore through a formation. The wellbore can be for an oil well, gas well, water well, or another well.

The drilling rig can have a substructure for supporting the drilling rig above a surface, such as the ground.

The drilling rig can include a base, which can be connected with the substructure.

The drilling rig can include a mast, which can be connected with the base. The mast can be a derrick.

The drilling rig can include a pipe handler engaged on the substructure.

The drilling rig can include a mud pump, which can be disposed below the substructure, such as on the surface. A drilling rig power source, such as a generator, can be in communication with the mud pump for providing power thereto.

The drilling rig can include drawworks disposed on the base and connected with cabling on the mast. A rotating head can be connected with the cabling and a blowout preventer.

A drill string can engage the blowout preventer and extend into the wellbore. The drill bit can be engaged with the drill string for drilling the wellbore.

The drilling rig can include a rig server having a rig processor and rig data storage for implementing rig operations. The rig server can be in communication with a network.

The network can be a satellite network, the internet, a cellular network, a combination of local area networks, a combination of wide area networks, another digital or analog network, a rig Wellsite Information Transfer Specification (WITS) communication network, an infrared communication network, a radio frequency communication network, another global communication network, or the like.

The drilling rig can include piping in fluid communication between the blowout preventer and a gas analyzer system for providing real-time measurement of a concentration of gases in the drilling fluid.

The gas analyzer system can be a motorized gas analyzer system, non-motorized gas analyzer system, or combinations thereof.

Real-time measurements taken by the gas analyzer system can include continuously or continually updated measurements. In one or more embodiments, each real-time measurement can be performed from about every five seconds to about every one minute, and can be continuously provided to a controller of the gas analyzer.

The concentration of the gases can be a concentration of dry gases, and can be measured in parts per million, parts per billion, a volumetric or weight percentage of individual gases relative to a total amount of liberated fluid, or another unit.

In one or more embodiments, the gases can be methane, ethane, propane, isobutane, butane, pentane, isopentane, neopentane, carbon dioxide, carbon monoxide, hydrogen sulfide, sulfur dioxide, hydrocarbon gas, hydrogen sulfide, helium, hydrogen, nitrogen, oxygen, or combinations thereof.

The drilling fluid can include liquids with entrained gases, oil based muds, water based muds, other drilling muds from the wellbore, water, air with entrained gases resulting from air drilling, other gaseous carriers entrained with gases resulting from air drilling, liquid and gas mixtures, vapor and gas mixtures, mixtures of gases, particulate and gas mixtures, or combinations thereof.

The gas analyzer system can include a sample chamber, such as a manifold. The sample chamber can have one or more sample inlets and one or more sample outlets. For example, the sample chamber can have one sample inlet and two sample outlets.

The sample chamber can be made of polymer, steel, aluminum, or any metal or metal alloy.

The sample inlets and sample outlets can be in fluid communication with the drilling fluid conduit, such as piping, to receive samples of the drilling fluid therefrom. In operation, the drilling fluid can flow via the drilling fluid conduit through the sample inlet and into the sample chamber. The drilling fluid conduit can have any flow rate.

The gas analyzer system can include a means for agitating and creating a vortex in the drilling fluid for liberating a portion of the drilling fluid from the sample chamber, forming a liberated fluid.

The means for agitating and creating a vortex can be disposed in the sample chamber or can be formed by the sample chamber. The means for agitating and creating a vortex can include the one or more sample outlets in the sample chamber, a direct current brushless motor, a pneumatic motor, an alternating current induction motor, a variable speed motor, an outlet with a regulated fluid level feature, or the like.

The gas analyzer system can include a gas capturing chamber in fluid communication with the sample chamber for receiving the liberated fluid from the sample chamber during agitation of the drilling fluid. For example, agitation via the means for agitating and creating a vortex can cause at least a portion of the gases, liquid, or combinations thereof in the drilling fluid to escape therefrom as the liberated fluid.

The gas capturing chamber can be made of polymer, steel, aluminum, or any metal or metal alloy.

The gas analyzer system can include a gas analyzer in fluid communication with the gas capturing chamber. The gas analyzer can be configured to provide real-time gas speciation of the liberated fluid. For example, the gas analyzer can be a gas chromatograph; a total gas analyzer; total hydrocarbon analyzer; totalizer; another instrument configured to measure different specific gases, such as carbon dioxide or hydrogen sulfide; another analytical instrument configured to determine speciation of gases; or the like.

In operation, the liberated fluid can flow into the gas capturing chamber and into the gas analyzer, allowing the gas analyzer to detect a speciation of the liberated fluid.

The gas analyzer system can include a suction pump, such as a 100 pounds per square inch (psi) suction pump, in fluid communication with the gas analyzer for pulling the liberated fluid from the sample chamber and into the gas analyzer. The suction pump can pump the liberated fluid at a flow rate ranging from about 1 standard cubic feet per hour (scfh) to about 10 scfh.

The gas analyzer system can include a filtration means in fluid communication between the gas capturing chamber and the gas analyzer. The filtration means can include desiccant chambers with calcium chloride, silica gel, DRIERITE®, or the like.

The gas analyzer system can include an exhaust port on the gas analyzer for releasing an analyzed fluid therefrom. The analyzed fluid can be released to the atmosphere or a containment tank. The analyzed fluid can be the liberated fluid that has been analyzed by the gas analyzer to produce the real-time gas speciation thereof.

The gas analyzer system can include an exhaust line on the gas capturing chamber for flowing a non-analyzed fluid from the gas capturing chamber to a drilling fluid storage chamber, back into the drilling fluid conduit, or combinations thereof. The drilling fluid storage chamber can be a pit, possum belly, storage tank, ditch, or the like. The non-analyzed fluid can flow from the gas capturing chamber at any rate.

In operation, a sample of the drilling fluid can be captured from the wellbore at a point in which the drilling fluid is homogenously mixed, and the liberated fluid, which can be a gas, liquid, or combinations thereof, can be formed therefrom.

The gas capturing chamber can receive the drilling fluid without requiring any pre-filtering or pretreatment of the drilling fluid in the drilling fluid conduit.

The filtering means can condition the liberated fluid, including removing moisture, contaminates, particulates, or combinations thereof from the liberated fluid. The filtering means can remove particulates having a diameter greater than five microns from the liberated fluid.

In one or more embodiments, the liberated fluid can be conditioned by desiccating moisture from a fluid conduit, mist separating using a mechanical separator, cooling using a heat exchanger, another conditioning means, or combinations thereof.

The gas capturing chamber can receive the liberated fluid from the filtering means through tubing, such as ¼ inch clear tubing having a ⅜ inch outer diameter and a length ranging from about 50 feet to about 75 feet.

The gas analyzer can analyze the liberated fluid to form measured gas values that indicate the speciation of the liberated fluid. The speciation can include an identification of elemental or chemical components, such as an identification of C-1 to C-5 hydrocarbons, carbon dioxide, carbon monoxide, hydrogen sulfide, helium, hydrogen, oxygen, nitrogen, argon, other gaseous elements or molecules compounds typically found in drilling fluid conduits, or combinations thereof.

The rig server, controller, or combinations thereof can transmit the measured gas values over the network to one or more client devices, which can be laptop computers, desktop computers, tablet computers, other computers, cellular phones, or the like.

Computer instructions on the client devices can allow the client devices to connect with the controller or a remote controller in communication with the controller to remotely monitor and control the gas analyzer system.

In one or more embodiments, the remote controller can be a pendant station that is in wired or wireless communication with the controller.

Each client device can have a client device processor in communication with a client device data storage having computer instructions to present an executive dashboard thereon.

The executive dashboard can provide for remote monitoring and control of the gas analyzer system. The client devices can enable users to simultaneously and remotely monitor and control multiple gas analyzer systems disposed at multiple locations via the executive dashboard.

The client devices can be used to receive, view, and store the measured gas values and other analysis information related to the liberated fluid, drilling fluid, and gas analyzer system. The client devices can also be used to provide control commands to the controller.

The rig server can be in communication with the network. The rig server can be located on or proximate the drilling rig, and can store and display on-demand analysis information related to the drilling fluid, liberated fluid, and gas analyzer system.

In one or more embodiments, the rig server can be a server, laptop computer, desktop computer, tablet computer, another computer, cellular phone, personal digital assistant, right mount server, programmable logic controller, or combinations thereof.

The rig server can include a rig processor in communication with a rig data storage, such as a hard drive, portable hard drive, flash drive, or other storage medium.

In one or more embodiments, the rig data storage can include computer instructions to provide an alarm to workers proximate to the drilling rig when analyzed gas samples show concentrations of components of the drilling fluid exceed preset limits.

The rig data storage can include computer instructions for broadcasting analysis information on components of the drilling fluid to one or more displays proximate the workers at the drilling rig, to client devices associated with each worker, to client devices associated with first responders, to client devices associated with other users, to the remote control, or combinations thereof.

In embodiments, the rig server can simultaneously transmit analysis information through two different gateway protocols via two different networks, such as a satellite network and a cellular data network.

In one or more embodiments, flow of the liberated fluid can be reversed, such that the gas capturing chamber flows the liberated fluid back into the drilling fluid conduit. For example, if the gas capturing chamber is clogged, reversing the flow of the liberated fluid can unclog the gas capturing chamber. Reversing the flow of the liberated fluid can be done remotely or locally.

In embodiments, a valve, such as a four-way valve, can be disposed proximate a top of the gas capturing chamber for reversing the flow of the liberated fluid.

In operation, when the four-way valve is in an off position, the gas capturing chamber can be in fluid communication with the gas analyzer, such that the liberated fluid flows from the gas capturing chamber into the gas analyzer.

When the four-way valve is in an on position, the gas capturing chamber can be in fluid communication with a compressed air source or ambient air, such that compressed air or ambient air can flow into the gas capturing chamber towards the drilling fluid conduit; thereby unclogging the gas capturing chamber.

In one or more embodiments, an electronic relay can be in communication with the four-way valve and the controller. The electronic relay can be programmed to move the four-way valve between the on position and the off position at predefined time intervals for unclogging the gas capturing chamber.

The electronic relay can be in communication with the client devices through the network, such that users can remotely turn the four-way valve to the on position and the off position. The electronic relay can be manually actuated at the drilling site.

Turning now to the figures, FIG. 1 depicts the drilling rig having continuous gas analysis according to one or more embodiments.

A drilling rig 300 can have a substructure 301 for supporting a base 302 connected with the substructure 301. The base 302 can support a mast 303 connected with the base 302.

A pipe handler 304 can be disposed on a portion of the drilling rig 300, such as on the substructure 301.

A mud pump 305 can be disposed below the substructure 301 for circulating drilling fluid. A drilling rig power source 311 can be in communication with the mud pump 305 for providing power thereto.

The drilling rig 300 can have drawworks 306 on the base 302. The drawworks 306 can be connected with cabling 310 in the mast 303. The drilling rig 300 can include a rotating head 33 connected with the cabling 310 and a blowout preventer 312.

A drill string 308 can engage the blowout preventer 312 and extend into a wellbore 3. A drill bit 11 can be engaged with the drill string 308 for drilling the wellbore 3 through a formation 313.

A rig server 64 for implementing rig operations can be in communication with a network 46. The rig server 64 can have a rig processor 6 and a rig data storage 7.

A drilling fluid conduit 14, such as piping, can be in fluid communication between the blowout preventer 312 and a portion of a gas analyzer system 5 for providing real-time measurement of a concentration of gases in the drilling fluid using a first gas analyzer 22a. The gas analyzer system 5 can be a non-motorized gas analyzer system.

In operation, a user can receive real-time measurements from the gas analyzer system 5, such as once a second or once every four seconds.

One or more client devices 44a and 44b can be in communication with the rig server 64, a portion of the gas analyzer system 5, or combinations thereof through the network 46, allowing users 45a and 45b to remotely monitor and control the gas analyzer system 5.

The users 45a and 45b can use the client devices 44a and 44b to simultaneously access the real-time measurements continually, 24 hours a day and 7 days a week.

The users 45a and 45b can also simultaneously access and view historical data and updated real-time measurements using the client devices 44a and 44b.

The client devices 44a and 44b can provide the users 45a and 45b with graphical representations, digital representations, or combinations thereof of the historical data, the updated real-time measurements, or combinations thereof.

The historical data can include previously taken measurements from the gas analyzer system 5, and the updated real-time measurements can include the most recently taken measurements from the gas analyzer system 5.

In operation, the gas analyzer system 5 can perform calculations on sensed data multiple times per second for greater accuracy and time resolution.

One or more embodiments of the drilling rig 300 can include a second gas analyzer 22b in communication with a motorized gas analyzer system 41 configured to be remotely controlled for real-time measurement of the concentration of the gases in the drilling fluid. The motorized gas analyzer system 41 can be in communication with the network 46 and in fluid communication with the drilling fluid conduit 14. For example, the motorized gas analyzer system 41 can be disposed in a possum belly.

The gas analyzers 22a and 22b can each be motorized, non-motorized, or combinations thereof.

In one or more embodiments, a remote controller 74 can be in wired or wireless communication with the gas analyzer system 5 and the motorized gas analyzer system 41, such as through the network 46, for remotely controlling the gas analyzer system 5 and the motorized gas analyzer system 41.

Figure 2:
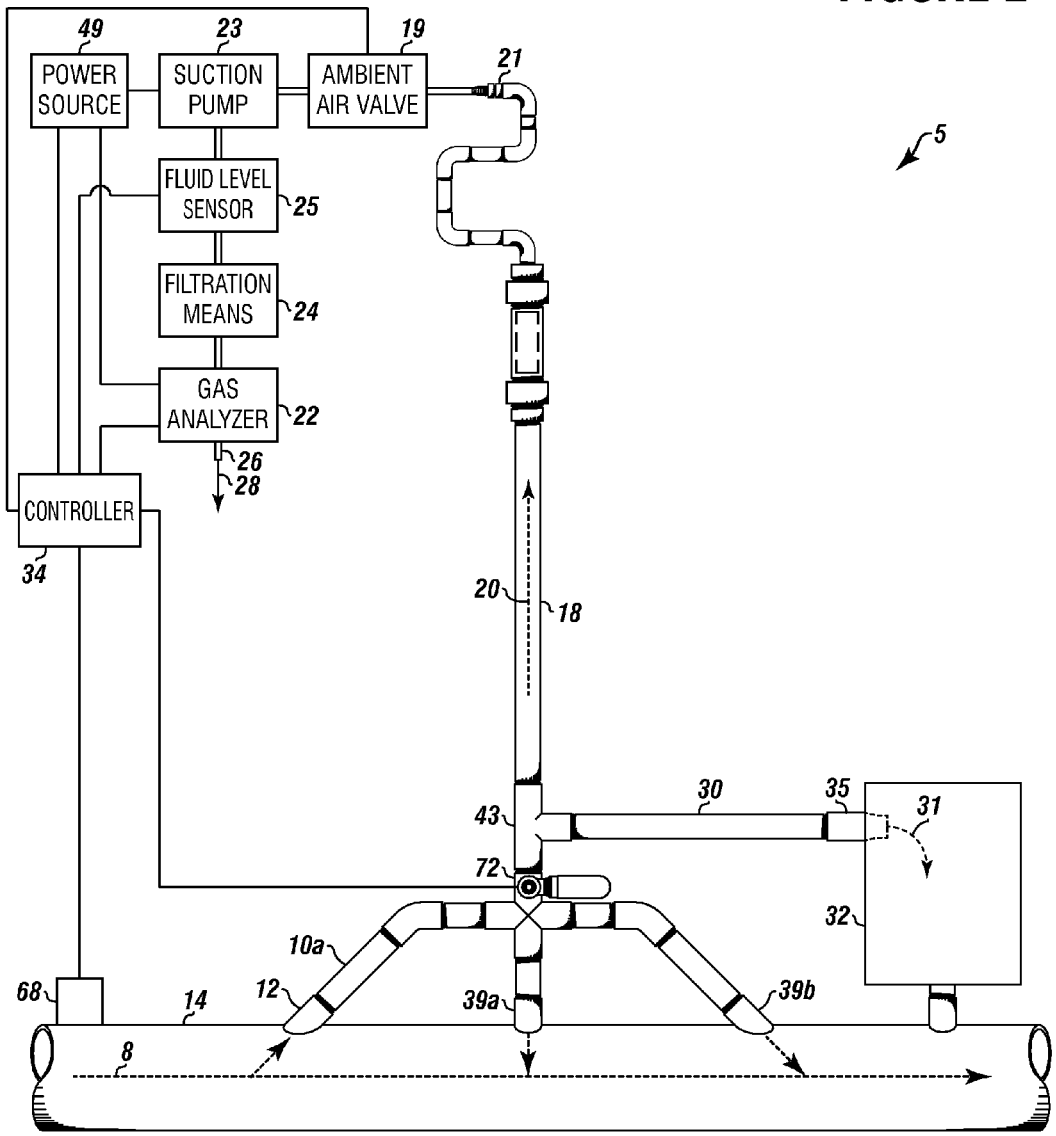
FIG. 2 depicts a detail of a gas analyzer system according to one or more embodiments.

FIG. 2 depicts a detail of the gas analyzer system according to one or more embodiments.

The gas analyzer system 5 can include a sample chamber 10a. The sample chamber 10a can have a sample inlet 12.

The sample inlet 12 can be in fluid communication with the drilling fluid conduit 14, which can be the piping from the drilling rig.

In operation, a drilling fluid 8 can flow from the drilling fluid conduit 14 into the sample inlet 12 and into the sample chamber 10a. The drilling fluid 8 can flow in the drilling fluid conduit 14 at a pressure of up to about 1000 psi.

The gas analyzer system 5 can include means for agitating and creating a vortex 39a and 39b, which can be return piping in fluid communication with the drilling fluid conduit 14, such as sample outlets of the sample chamber 10a.

The means for agitating and creating a vortex 39a and 39b can operate to form a vortex in the drilling fluid 8 within the sample chamber 10a, which can separate a portion of gas therefrom, forming a liberated fluid 20.

The liberated fluid 20 can flow from the sample chamber 10a through a valve 72, while the remaining drilling fluid 8 can flow back into the drilling fluid conduit 14 via the means for agitating and creating a vortex 39a and 39b.

The valve 72 can be in communication with the controller 34 for closing off the sample chamber 10a upon command.

During agitation of the drilling fluid 8, the liberated fluid 20 can flow from the valve 72 and through a t-fitting 43 and into a gas capturing chamber 18, or through the t-fitting 43 into an exhaust line 30 for flowing a non-analyzed fluid 31 to a drilling fluid storage chamber 32, back into the drilling fluid conduit 14, or both. The non-analyzed fluid 31 can be portions of the liberated fluid 20 that are not analyzed by the gas analyzer system 5. The drilling fluid storage chamber 32 can be a pit, possum belly, storage tank, ditch, or the like.

In one or more embodiments, a venturi nozzle 35 can be on the exhaust line 30 for flowing the non-analyzed fluid 31 from the gas capturing chamber 18 to the drilling fluid storage chamber 32, drilling fluid conduit 14, or both.

A suction pump 23 can be in fluid communication between the gas capturing chamber 18 and a gas analyzer 22. The suction pump 23 can pull the liberated fluid 20 from the gas capturing chamber 18 and into the gas analyzer 22.

A semipermeable membrane 21 can be disposed between the suction pump 23 and the gas capturing chamber 18, such as within a portion of the gas capturing chamber 18, to provide additional filtering to the liberated fluid 20. The semipermeable membrane 21 can be made of a material configured to separate water or vapor from the liberated fluid 20, such as a thin film composite membrane, which can be constructed from two or more layers of materials.

A filtration means 24 can be in fluid communication between the gas capturing chamber 18 and the gas analyzer 22 for conditioning the liberated fluid 20. Conditioning the liberated fluid 20 can include drying the liberated fluid 20 and removing particulates and other contaminates from the liberated fluid 20.

The gas analyzer 22 can be in fluid communication with the gas capturing chamber 18 and configured to provide real-time gas speciation of the liberated fluid 20.

An exhaust port 26 on the gas analyzer 22 can release an analyzed fluid 28 therefrom.

The controller 34 can be in communication with the gas analyzer 22 for controlling the gas analyzer 22.

A power supply 49 can be in communication with the controller 34, the gas analyzer 22, and the suction pump 23 for providing power thereto. The power supply 49 can be a 120 volt power source, a solar power source, an AC/DC switching power supply, a generator, a wind turbine, or another power supply.

The controller 34 can be in communication with the network for communicating with the rig server, the client devices, the remote controller, the motorized gas analyzer system, or combinations thereof.

One or more embodiments can include a sensor 68 disposed adjacent the sample inlet 12 and in communication with the controller 34 for providing sensor values to the controller 34. The sensor 68 can be a flow sensor, pressure sensor, temperature sensor, sensor configured to measure viscosity of the drilling fluid 8, sensor configured to measure a percent of solids in the drilling fluid 8, or another type of sensor.

The controller 34 can use the sensor values to determine when the valve 72 needs to be shut, such as in emergencies. For example, when the sensor 68 is a pressure sensor the controller 34 can determine that the valve 72 needs to be shut when an over-pressurization exists; thereby stopping flow of the liberated gas 20 into the gas capturing chamber 18.

One or more embodiments can include a fluid level sensor 25 disposed between the suction pump 23 and the filtration means 24, and in communication with the controller 34 for sensing when liquid in the liberated fluid 20 rises above a preset limit. The fluid level sensor 25 can be adjacent the filtration means 24. The fluid level sensor 25 can transmit sensed fluid level values to the controller 34.

For example, the fluid level sensor 25 can include a chamber configured to collect fluid from the liberated fluid 20, and when the liquid collected from the liberated fluid 20 reaches the preset limit the fluid level sensor 25 can transmit a signal to the controller 34. The controller 34 can then open an ambient air valve 19 for drawing in ambient air instead of allowing flow of the liberated fluid 20 from the gas capturing chamber 18.

The ambient air valve 19 can be in fluid communication between the gas capturing chamber 18 and the suction pump 23. As such, liquid in the liberated fluid 20 can be prevented from flowing into the gas analyzer 22; thereby avoiding damage to the gas analyzer 22.

Figure 3:
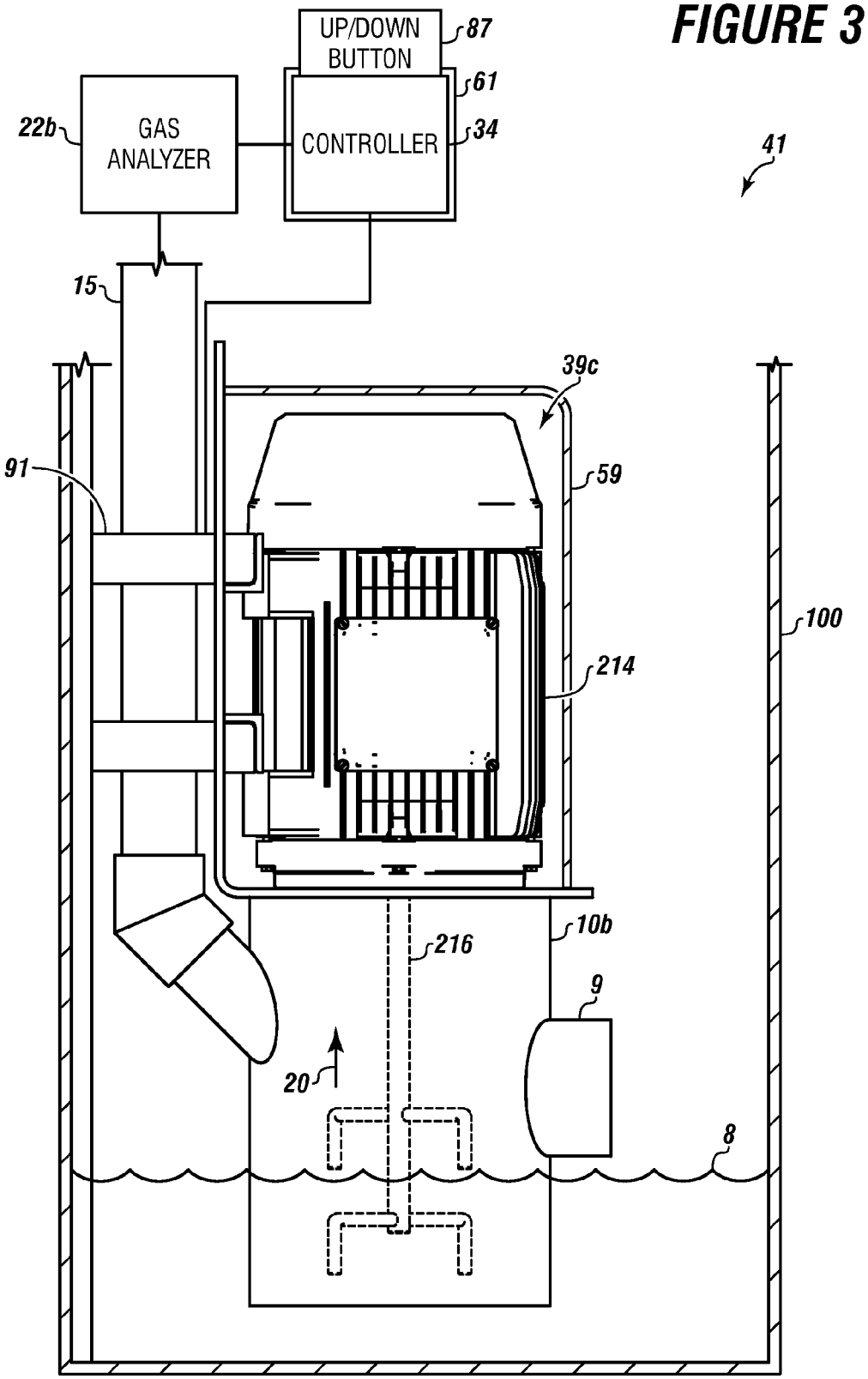
FIG. 3 depicts a motorized gas analyzer system according to one or more embodiments.

FIG. 3 depicts the motorized gas analyzer system according to one or more embodiments.

The motorized gas analyzer system 41 can include the sample chamber 10b having the means for agitating and creating a vortex 39c. The means for agitating and creating a vortex 39c can include a motor 214 connected with an agitator shaft 216.

In one or more embodiments, the motor 214 can be a direct current brushless motor, a pneumatic motor, an alternating current induction motor, a variable speed motor, or the like.

The means for agitating and creating a vortex 39c can include a spout 9 with a regulated fluid level feature, such as a ballast tank 15 under positive pressure for regulating a fluid level of the drilling fluid 8. The spout 9 can allow the drilling fluid 8 to exit the sample chamber 10b when the drilling fluid 8 rises above a preset limit.

In one or more embodiments, the means for agitating and creating a vortex 39c can be housed in an explosion-proof housing 59.

A lifting device 91, such as a motorized lifting device or agitator stand, can be attached to a portion of the motorized gas analyzer system 41 and to a tank 100 within which the motorized gas analyzer system 41 is disposed. The tank 100 can be the drilling fluid storage chamber, pit, possum belly, storage tank, ditch, or the like.

The lifting device 91 can operate to raise and lower the sample chamber 10b, the motor 214, and the agitator shaft 216 to ensure that the drilling fluid 8 in the sample chamber 10b is at a proper level for liberation of the gases therefrom; thereby providing for consistent and constant analysis of the liberated fluid 20. For example, the lifting device 91 can include a crank for raising and lowering the sample chamber 10b.

The motorized gas analyzer system 41 can include the gas analyzer 22b in fluid communication therewith for analyzing the liberated fluid 20.

The controller 34 can have an up/down button 87 for communicating with the lifting device 91 to raise and lower the sample chamber 10b. The controller 34 can be housed in a bullet-proof and water-tight housing 61, which can be made of steel or the like.

Figure 4A:
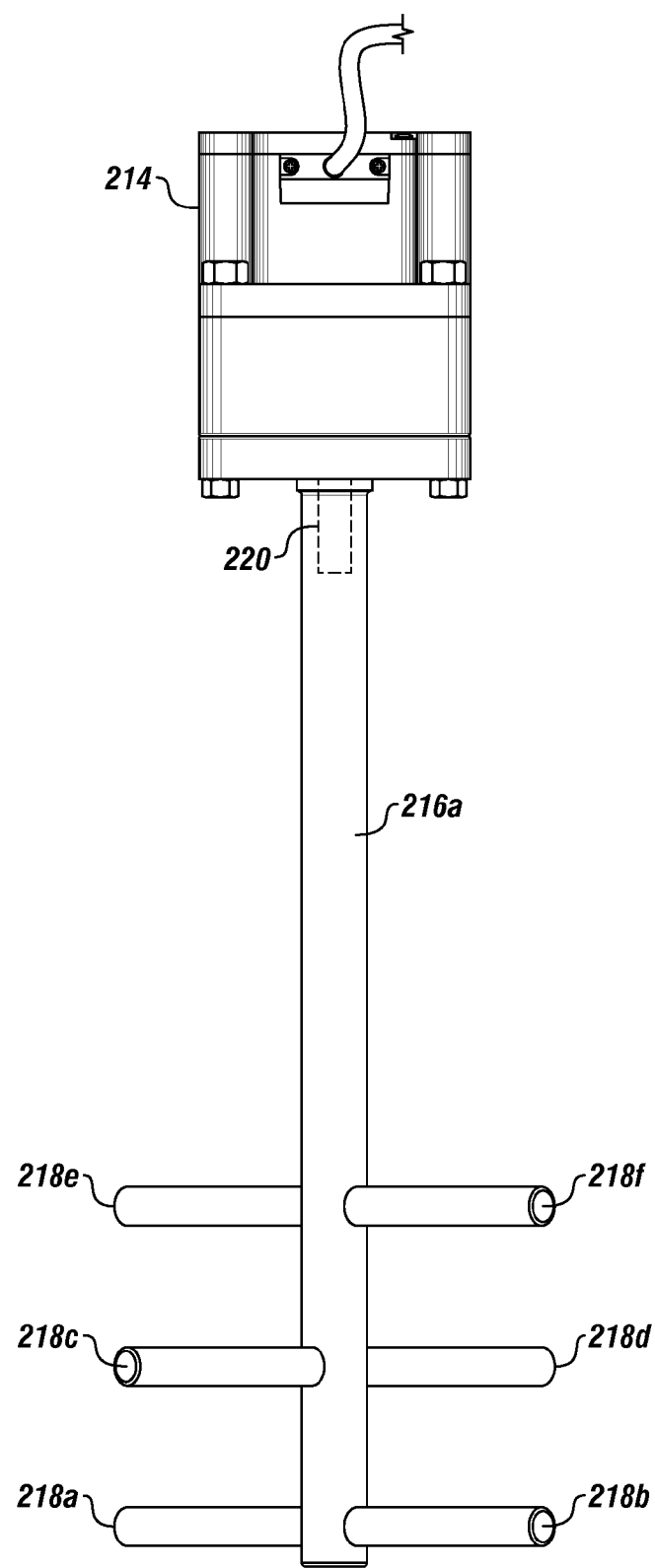
FIGS. 4A, 4B, and 4C depict detail views of a portion of a means for agitating and creating a vortex according to various embodiments.

FIG. 4A depicts a detail view of a portion of the means for agitating and creating a vortex according to one or more embodiments.

The motor 214 can be engaged with the agitator shaft 216a. The motor 214 can be partially inserted into the agitator shaft 216a, such as within an inner chamber 220 of the agitator shaft 216a.

The inner chamber 220 can be configured to receive a portion of the motor 214, allowing the motor 214 to rotate the agitator shaft 216a.

The agitator shaft 216a can have one or more pairs of blades 218a, 218b, 218c, 218d, 218e, and 218f. The blades 218a and 218b can form a pair of blades, the blades 218c and 218d can form a pair of blades, and the blades 218e and 218f can form a pair of blades.

Each pair of blades can be offset from adjacent pairs of blades by ninety degrees. For example, the pair of blades 218c and 218d can be offset from the pair of blades 218a and 218b by ninety degrees and from the pair of blades 218e and 218f by ninety degrees. Each blade 218a-218f can be a rubber or metal cylinder.

Figure 4B:
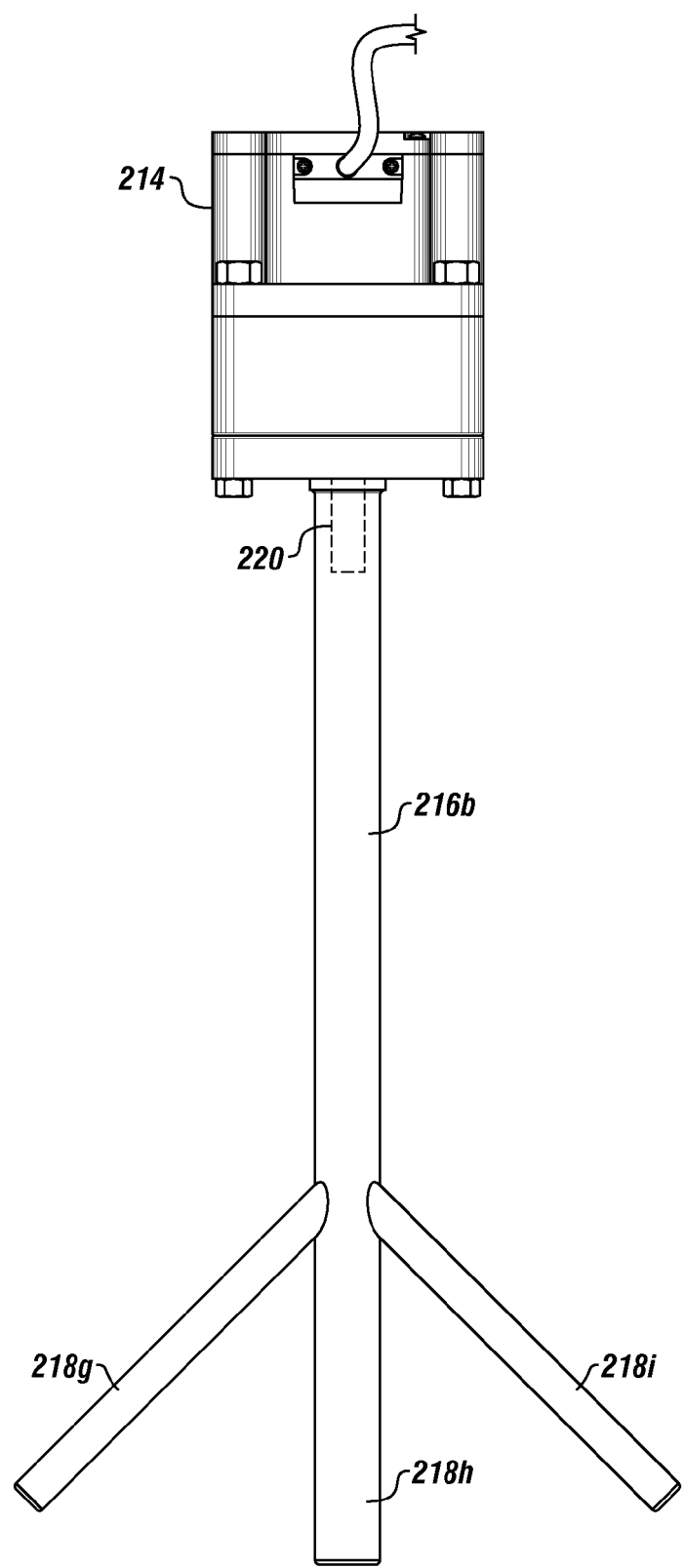

FIG. 4B depicts a detail view of a portion of the means for agitating and creating a vortex according to one or more embodiments.

The motor 214 can be engaged with the agitator shaft 216b, such as within the inner chamber 220 of the agitator shaft 216b.

The agitator shaft 216b can have one or more blades 218g, 218h, and 218i, which can be formed in a crow's foot configuration. Each blade 218g-218i can be a rubber or metal cylinder.

Figure 4C:
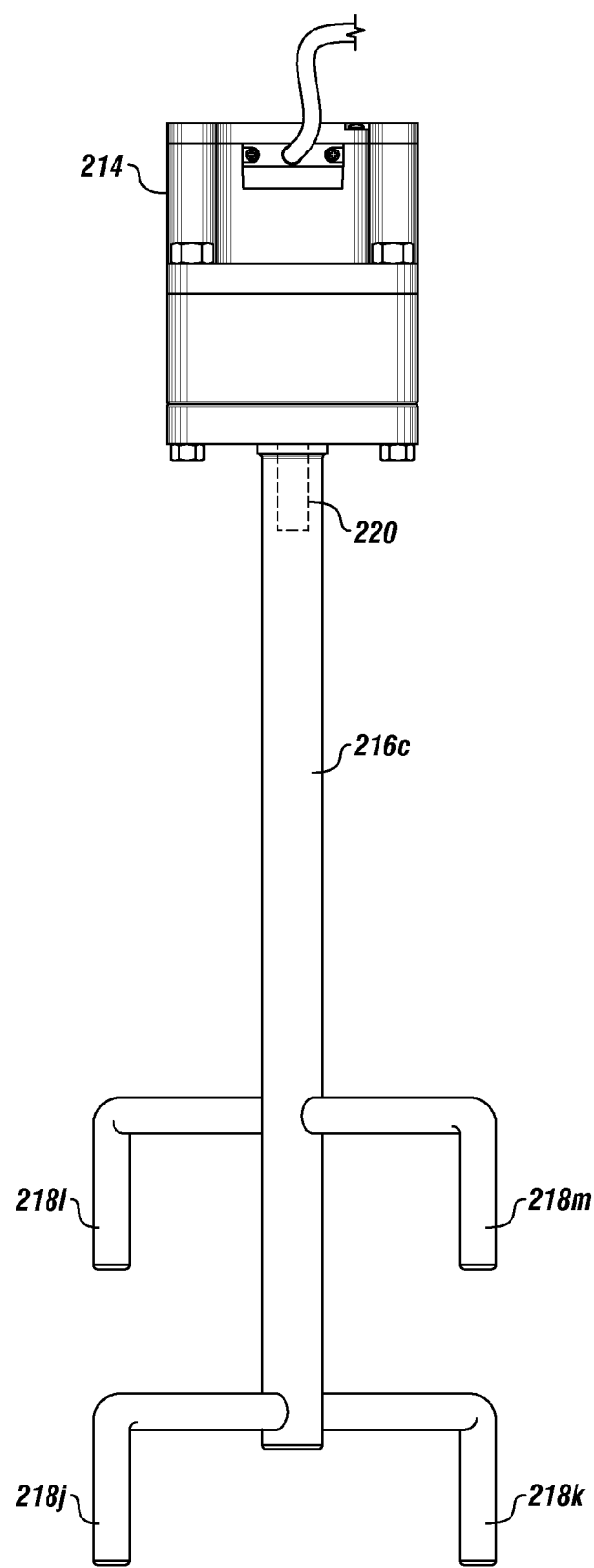

FIG. 4C depicts a detail view of a portion of the means for agitating and creating a vortex according to one or more embodiments.

The motor 214 can be engaged with the agitator shaft 216c, such as within an inner chamber 220 of the agitator shaft 216c.

The agitator shaft 216c can have one or more blades 218j, 218k, 218l, and 218m arranged in a pitch fork configuration. Each blade 218j-218m can be a rubber or metal cylinder.

Figure 5:
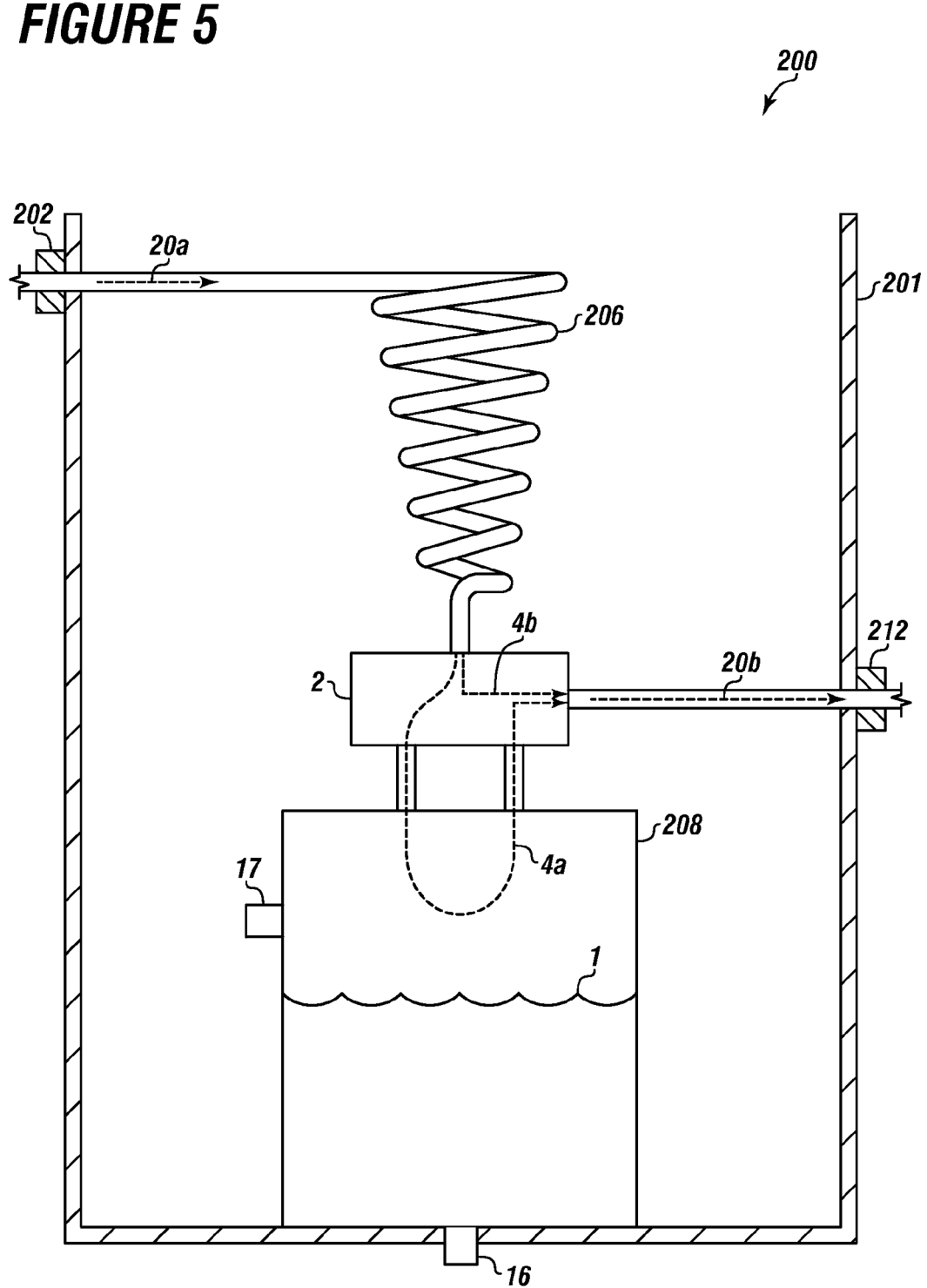
FIG. 5 depicts a detail of a portion of a filtration means according to one or more embodiments.

FIG. 5 depicts a portion of the filtration means according to one or more embodiments.

The filtration means can include a cooler/dryer 200 configured to refrigerate the liberated fluid 20a, causing condensed liquid 1 to drop out from the liberated fluid 20a.

The cooler/dryer 200 can include a housing 201 with an inlet 202 for receiving the liberated fluid 20a from the sample chamber, such as when the liberated fluid 20a is at an elevated temperature.

A cooling coil 206, which can be made of copper, can be in fluid communication with the inlet 202, allowing the liberated fluid 20a to enter the cooling coil 206 and cool while the liberated fluid 20a passes to a drop out chamber 208. The cooling coil 206 can have a length sufficient to allow the liberated fluid 20a to cool enough to allow water or other liquids to condense therefrom.

The drop out chamber 208 can receive cooled liberated fluid 20b and the condensed liquid 1 therefrom.

A dry gas out 212 can allow the liberated fluid 20b to pass from the drop out chamber 208 to the gas analyzer.

One or more embodiments can include a maintenance valve arrangement 2, such as a four way valve or a combination of valves. The maintenance valve arrangement 2 can be opened to allow the liberated fluid 20b to flow via a first flow path 4a and allow the condensed liquid 1 to collect in the drop out chamber 208.

The maintenance valve arrangement 2 can be closed to allow the liberated fluid 20b to flow via a second flow path 4b to bypass the drop out chamber 208, allowing the drop out chamber 208 to be drained.

The drop out chamber 208 can have a drain valve 16 for draining the condensed liquid 1 and an air valve 17 for receiving ambient or pressurized air to allow flow of the condensed liquid 1 from the drop out chamber 208.

Figure 6A:
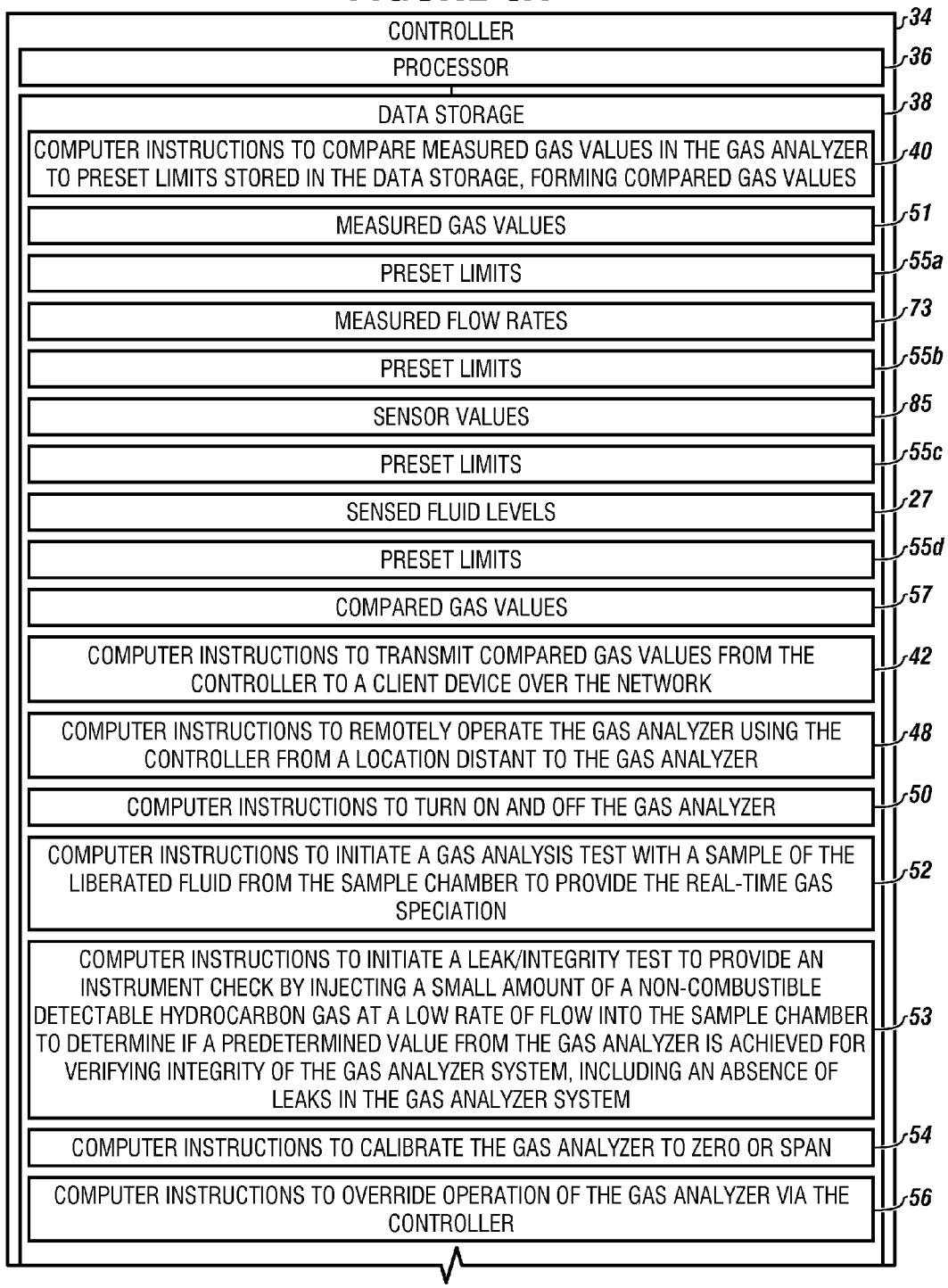
FIGS. 6A and 6B depict a detail of a controller according to one or more embodiments.
Figure 6B:
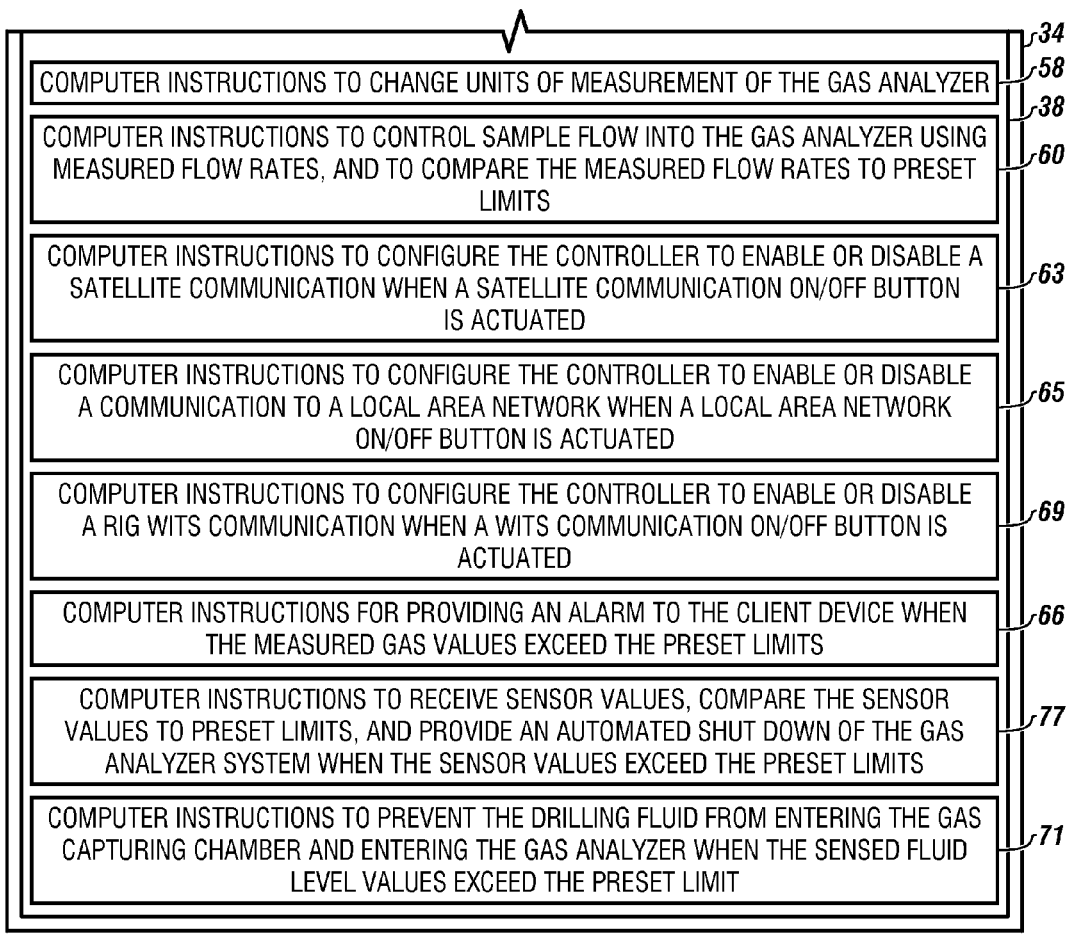

FIGS. 6A and 6B depict a detail of the controller according to one or more embodiments.

The controller 34 can include a processor 36 in communication with a data storage 38.

The data storage 38 can include computer instructions to compare measured gas values in the gas analyzer to preset limits stored in the data storage, forming compared gas values 40.

The measured gas values 51, preset limits 55a, and compared gas values 57 can be stored in the data storage 38.

The data storage 38 can include computer instructions to transmit compared gas values from the controller to a client device over the network 42.

The data storage 38 can include computer instructions to remotely operate the gas analyzer using the controller from a location distant to the gas analyzer 48.

The data storage 38 can include computer instructions to turn on and off the gas analyzer 50.

The data storage 38 can include computer instructions to initiate a gas analysis test with a sample of the liberated fluid from the sample chamber to provide the real-time gas speciation 52.

The data storage 38 can include computer instructions to initiate a leak/integrity test to provide an instrument check by injecting a small amount of a non-combustible detectable hydrocarbon gas at a low rate of flow into the sample chamber to determine if a predetermined value from the gas analyzer is achieved for verifying integrity of the gas analyzer system, including an absence of leaks in the gas analyzer system 53.

The non-combustible detectable hydrocarbon gas can be methane, propane, other gases, or mixtures thereof. The leak/integrity test can be implemented using 10 pound or 20 pound bottles of the non-combustible detectable hydrocarbon gas, or any other sized bottle.

The data storage 38 can include computer instructions to calibrate the gas analyzer to zero or span 54.

For example, a client input value with a known value of gas can be used to calibrate the gas analyzer.

The data storage 38 can include computer instructions to override operation of the gas analyzer via the controller 56.

For example, the gas analyzer can be overridden for safety during replacement of sensors.

The data storage 38 can include computer instructions to change units of measurement of the gas analyzer 58.

For example, the units can be changed between parts per million, parts per billion, percent by weight, percent by volume, or the like.

The data storage 38 can include computer instructions to control sample flow into the gas analyzer using measured flow rates, and to compare the measured flow rates to preset limits 60.

For example, the sample flow can be controlled by opening, closing, or adjusting one or more valves.

The measured flow rates 73 and the preset limits 55*b* can be stored in the data storage 38.

The data storage 38 can include computer instructions to configure the controller to enable or disable a satellite communication when a satellite communication on/off button is actuated 63.

For example, the satellite communication on/off button can be actuated on the remote controller.

The data storage 38 can include computer instructions to configure the controller to enable or disable a communication to a local area network when a local area network on/off button is actuated 65.

For example, the local area network on/off button can be actuated on the remote controller.

The data storage 38 can include computer instructions to configure the controller to enable or disable a rig WITS communication when a WITS communication on/off button is actuated 69.

For example, the WITS communication on/off button can be actuated on the remote controller.

The data storage 38 can include computer instructions for providing an alarm to the client device when the measured gas values exceed the preset limits 66.

The data storage 38 can include computer instructions to receive sensor values, compare the sensor values to preset limits, and provide an automated shut down of the gas analyzer system when the sensor values exceed the preset limits 77.

For example, the gas analyzer system can be automatically shut down by closing one or more valves in response to sensor values.

The sensor values 85 and the preset limits 55*c* can be stored in the data storage 38.

The data storage 38 can include computer instructions to prevent the drilling fluid from entering the gas capturing chamber and entering the gas analyzer when the sensed fluid level values exceed the preset limit 71.

For example, the drilling fluid can be prevented from entering the gas capturing chamber and the gas analyzer by closing the ambient air valve. The sensed fluid levels 27 and the preset limits 55*d* can be stored in the data storage 38.

Figure 7:
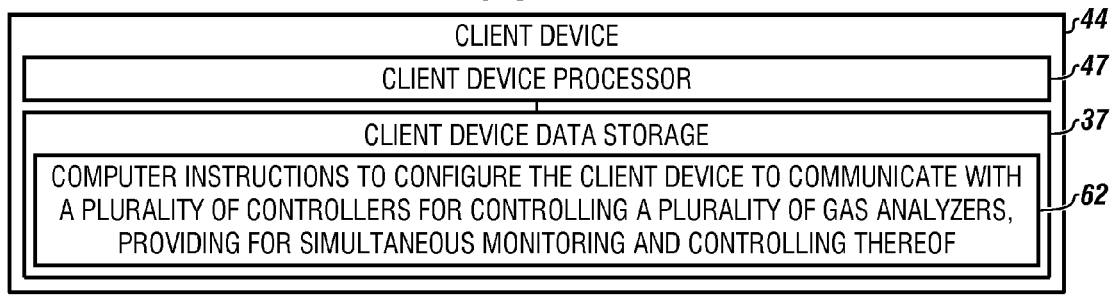
FIG. 7 depicts a client device according to one or more embodiments.

FIG. 7 depicts the client device according to one or more embodiments.

The client device 44 can include a client device processor 47 in communication with a client device data storage 37.

The client device data storage 37 can include computer instructions to configure the client device to communicate with a plurality of controllers for controlling a plurality of gas analyzers, providing for simultaneous monitoring and controlling thereof 62.

Figure 8A:
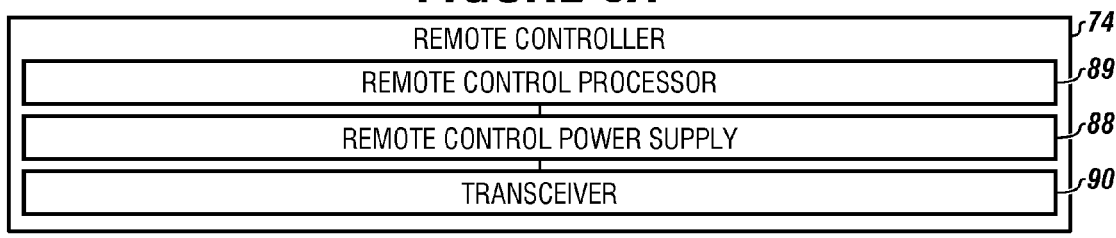
FIGS. 8A and 8B depict a remote controller according to one or more embodiments.
Figure 8B:
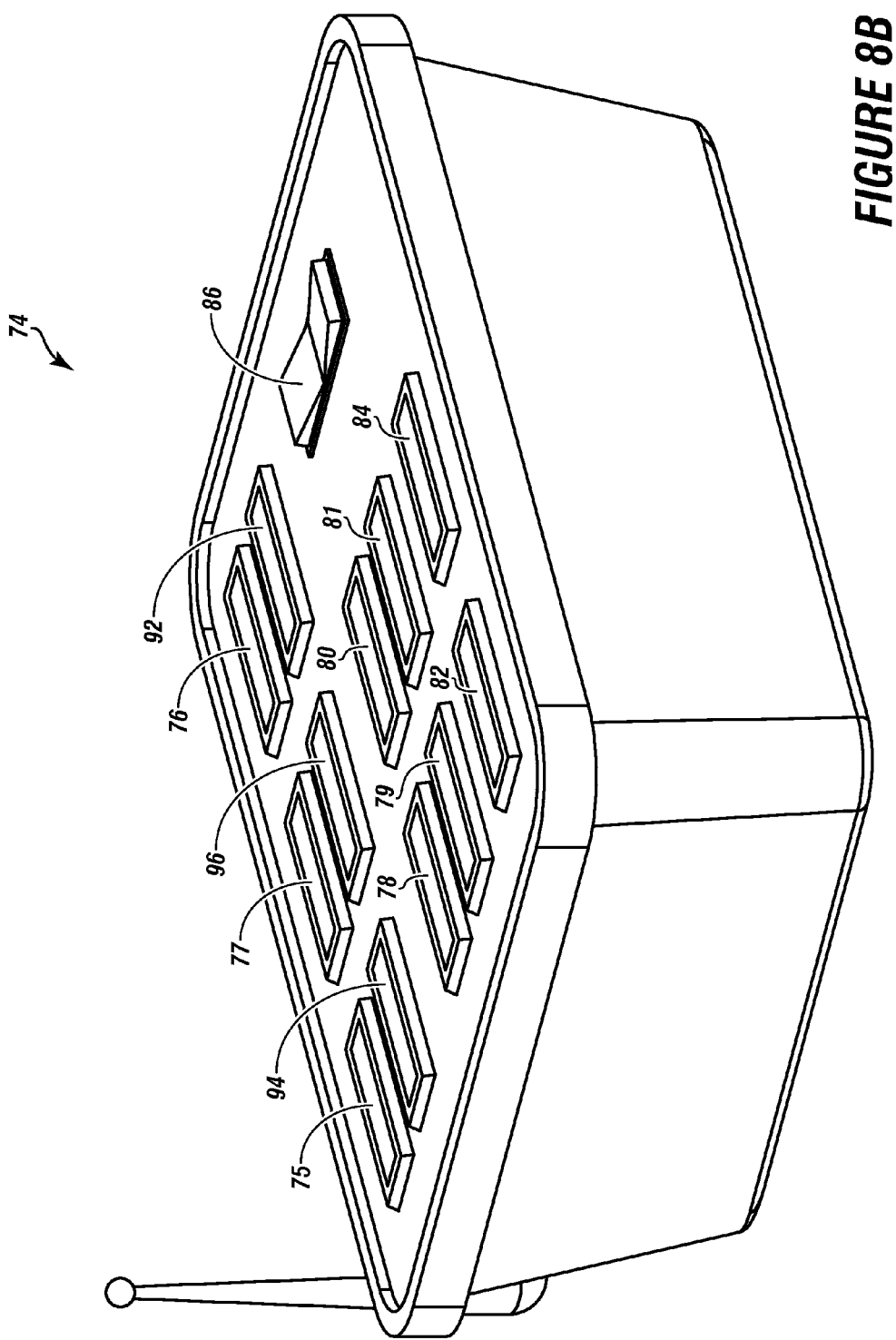

FIGS. 8A and 8B depict the remote controller according to one or more embodiments.

The remote controller 74 can include a remote control processor 89 and a transceiver 90 in communication with the remote control processor 89.

The transceiver 90 can be configured to communicate with the controller, such as through the network. In one or more embodiments, the transceiver 90 can be an infrared communication device, a client server device, a cellular communication device, a radio frequency communication device, or an internet based communication device.

The remote controller 74 can include a remote control power supply 88, such as a battery.

The remote controller 74 can include buttons configured to communicate with the controller via the transceiver 90 for executing the computer instructions in the data storage of the controller.

The buttons on the remote controller 74 can include a remote on/off button 75 configured to turn on and off the remote controller 74; an on/off button 76 configured to initiate operation of the means for agitating and creating a vortex; an on/off gas analyzer button 77 for turning the gas analyzer on and off; a start gas analysis button 78 for initiating the real-time gas speciation; a start leak/integrity test button 79 for initiating a leak integrity test; a start calibration to zero button 80 for initiating calibration of the gas analyzer at zero; a start calibration to span button 81 for initiating calibration of the gas analyzer to span; a safety override button 82 for shutting the gas analyzer system down by closing one or more valves; a change output units of measure button 84 for changing units of measurement of the gas analyzer; a control sample flow button 86 for opening, closing, or adjusting one or more valves to control flow of the liberated fluid; a satellite communication on/off button 92 for enabling or disabling a satellite communication; a local area network on/off button 94 for enabling or disabling communication with a local area network; and a WITS communication on/off button 96 for enabling or disabling a rig WITS communication.

The rig WITS communication can be used for connecting WITS software for transfer of data from the gas analyzer to the rig server.

While these embodiments have been described with emphasis on the embodiments, it should be understood that within the scope of the appended claims, the embodiments might be practiced other than as specifically described herein.

What is claimed is:

1. A drilling rig for drilling a wellbore through a formation and providing continuous gas analysis, the drilling rig comprising:
   a. a rig server comprising a rig processor and a rig data storage for implementing rig operations, wherein the rig server is in communication with a network; and
   b. a drilling fluid conduit in fluid communication between a blowout preventer of the drilling rig and a gas analyzer system, wherein the gas analyzer system is configured for real-time measurement of a concentration of gases in a drilling fluid within the drilling fluid conduit, and wherein the gas analyzer system comprises:
- (i) a sample chamber comprising a sample inlet in fluid communication with the drilling fluid conduit, wherein the drilling fluid flows directly from the drilling fluid conduit into the sample inlet and into the sample chamber;
- (ii) means for agitating and creating a vortex in the drilling fluid disposed in the sample chamber or formed by the sample chamber wherein the means for agitating and creating a vortex forms a liberated fluid from the drilling fluid;
- (iii) a gas capturing chamber in selective fluid communication with the sample chamber for receiving the liberated fluid from the sample chamber during agitation of the drilling fluid, wherein the gas capturing chamber allows the liberated fluid to flow at a lower pressure than the drilling fluid;
- (iv) a gas analyzer in fluid communication with the gas capturing chamber, wherein the gas analyzer is configured to provide real-time gas speciation of the liberated fluid;
- (v) a suction pump in fluid communication with the gas analyzer for pulling the liberated fluid from the sample chamber and into the gas analyzer;
- (vi) a filtration means in fluid communication between the gas capturing chamber and the gas analyzer, wherein the filtration means comprising a cooler/dryer is configured to refrigerate the liberated fluid and cause condensed liquid to drop out from the liberated fluid;
- (vii) an exhaust port on the gas analyzer for releasing an analyzed fluid therefrom;
- (viii) an exhaust line on the gas capturing chamber for flowing a non-analyzed fluid from the gas capturing chamber to a drilling fluid storage chamber or to the drilling fluid conduit; and
- (ix) a venturi nozzle in the exhaust line for flowing the non-analyzed fluid from the gas capturing chamber to the drilling fluid storage chamber or the drilling fluid conduit.

2. The drilling rig of claim 1, where the drilling rig further comprises:
- a. a substructure, a base connected with the substructure, a mast connected with the base, and a pipe handler engaged on the substructure;
- b. a mud pump below the substructure and a drilling rig power source in communication with the mud pump;
- c. drawworks on the base, cabling connected with the drawworks and the mast, and a rotating head connected with the cabling and the blowout preventer; and
- d. drill string engaging the blowout preventer and extending into the wellbore, wherein a drill bit is engaged with the drill string.

3. The drilling rig of claim 1, wherein the gases in the drilling fluid are a member of a group consisting of: methane, ethane, propane, isobutane, butane, pentane, isopentane, neopentane, carbon dioxide, carbon monoxide, hydrogen sulfide, sulfur dioxide, and combinations thereof.

4. The drilling rig of claim 1, further comprising a second gas analyzer in communication with a motorized gas analyzer system configured for remote control for real-time measurement of the concentration of the gases in the drilling fluid, wherein the motorized gas analyzer system is in communication with the network.

5. The drilling rig of claim 1, wherein the network is a satellite network, another global communication network, the internet, a cellular network, combinations of local area networks, combinations of wide area networks, other digital or analog networks, or combinations thereof.

6. The drilling rig of claim 1, wherein the drilling rig is a land based rig, a semisubmersible rig, a portable rig with self-propulsion, a skid mounted rig, a jack-up rig, a tension leg platform, a drilling ship, a deep draft cassion vessel rig, a drilling rig for pneumatic drilling, a drilling rig for foam drilling, a drilling rig for hydraulic drilling, a drilling rig for oil based mud drilling, a drilling rig for water based mud drilling, or a single or simultaneously dual lifting drilling rig.

7. The drilling rig of claim 1, wherein the means for agitating and creating a vortex is housed in an explosion-proof housing.

8. The drilling rig of claim 1, wherein the cooler/dryer comprises:
- a. a housing with an inlet for receiving the liberated fluid from the sample chamber;
- b. a cooling coil connected to the inlet, allowing the liberated fluid to enter the cooling coil and cool while the liberated fluid passes therethrough to a drop out chamber, wherein the drop out chamber receives the liberated fluid and condensed liquid; and
- c. a dry gas out configured to allow the liberated fluid to pass from the drop out chamber to the gas analyzer.

9. The drilling rig of claim 8, further comprising a maintenance valve arrangement in fluid communication with the cooling coil, wherein the maintenance valve arrangement is openable to allow the liberated fluid to flow via a first flow path and the condensed liquid to collect in the drop out chamber, wherein the maintenance valve arrangement is closable to allow the liberated fluid to flow via a second flow path to bypass the drop out chamber, and wherein the drop out chamber comprises a drain valve for draining the condensed liquid and an air valve for allowing draining of the condensed liquid by receiving ambient or pressurized air.

10. The drilling rig of claim 1, wherein the means for agitating and creating a vortex comprises a motor partially inserted into an agitator shaft, wherein the agitator shaft comprises blades.

11. The drilling rig of claim 10, wherein:
- a. the blades are arranged in pairs, and wherein each pair is offset from adjacent pairs;
- b. the blades are arranged in a crow's foot configuration; or
- c. the blades are arranged in a pitchfork configuration.

12. The drilling rig of claim 10, wherein each blade is a rubber or metal cylinder, and wherein the agitator shaft further comprises an inner chamber for receiving a portion of the motor.

13. The drilling rig of claim 1, further comprising a semipermeable membrane disposed between the suction pump and the gas capturing chamber to provide additional filtering before the liberated fluid reaches the gas analyzer.

14. The drilling rig of claim 1, further comprising:
- a. a controller in communication with the gas analyzer, wherein the controller comprises:
  - (i) a processor in communication with a data storage;
  - (ii) computer instructions in the data storage to compare measured gas values in the gas analyzer to preset limits stored in the data storage;

(iii) computer instructions in the data storage to transmit compared gas values from the controller to a client device over the network; and (iv) computer instructions in the data storage to remotely operate the gas analyzer using the controller; and b. a power supply in communication with the controller, the gas analyzer, and the suction pump.

15. The drilling rig of claim 14, wherein the controller further comprises: an up/down button for communicating with a motorized lifting device attached to the sample chamber to raise and lower the sample chamber and ensure that the drilling fluid in the sample chamber is at a level that ensures liberation of the gases therefrom.

16. The drilling rig of claim 14, wherein the controller is housed in a bullet-proof and water-tight housing.

17. The drilling rig of claim 14, wherein the controller further comprises:
   a. computer instructions to turn on and off the gas analyzer;
   b. computer instructions to initiate a gas analysis test with a sample of the liberated fluid from the sample chamber to provide the real-time gas speciation;
   c. computer instructions to initiate a leak/integrity test by injecting a non-combustible detectable hydrocarbon gas into the sample chamber to determine if a predetermined value from the gas analyzer is achieved for verifying integrity of the gas analyzer system including an absence of leaks in the gas analyzer system;
   d. computer instructions to calibrate the gas analyzer to zero or span;
   e. computer instructions to override operation of the gas analyzer via the controller;
   f. computer instructions to change units of measurement of the gas analyzer;
   g. computer instructions to control sample flow into the gas analyzer using measured flow rates, and to compare the measured flow rates to preset limits;
   h. computer instructions to configure the controller to enable or disable a satellite communication when a satellite communication on/off button is actuated;
   i. computer instructions to configure the controller to enable or disable a communication to a local area network when a local area network on/off button is actuated; and
   j. computer instructions to configure the controller to enable or disable a rig communication when a communication on/off button is actuated.

18. The drilling rig of claim 14, further comprising computer instructions in the client device to configure the client device to communicate with a plurality of controllers that control a plurality of gas analyzers for simultaneous monitoring and controlling thereof.

19. The drilling rig of claim 14, further comprising a motorized gas analyzer system configured for remote control real-time measuring of the concentration of the gases in the drilling fluid, wherein the motorized gas analyzer system is in communication with the controller.

20. The drilling rig of claim 14, further comprising computer instructions in the data storage for providing an alarm to the client device when the measured gas values exceed the preset limits.

21. The drilling rig of claim 14, further comprising a sensor disposed adjacent the sample inlet and in communication with the controller, wherein the data storage further comprises computer instructions to receive sensor values, compare the sensor values to preset limits, and provide an automated shut down of the gas analyzer system when the sensor values exceed the preset limits by closing a valve for closing off the sample chamber upon command.

22. The drilling rig of claim 14, further comprising a remote controller comprising:
   a. a remote control processor;
   b. a transceiver in communication with the remote control processor and the controller;
   c. a remote control power supply; and
   d. buttons on the remote controller configured to communicate with the controller via the transceiver for executing the computer instructions in the data storage of the controller.

23. The drilling rig of claim 22, wherein the button comprises:
   a. a remote on/off button configured to turn on and off the remote control;
   b. an on/off button configured to initiate operation of the means for agitating and creating a vortex;
   c. an on/off gas analyzer button for turning the gas analyzer on and off;
   d. a start gas analysis button for initiating the real-time gas speciation;
   e. a start leak/integrity test button for initiating a leak integrity test;
   f. a start calibration to zero button for initiating calibration of the gas analyzer at zero;
   g. a start calibration to span button for initiating calibration of the gas analyzer to span;
   h. a safety override button for closing one or more valves;
   i. a change output units of measure button for changing units of measurement of the gas analyzer;
   j. a control sample flow button for closing one or more valves;
   k. a satellite communication on/off button for enabling or disabling a satellite communication;
   l. a local area network on/off button for enabling or disabling communication with a local area network; and
   m. a communication on/off button for enabling or disabling a rig communication.

24. The drilling rig of claim 23, wherein the transceiver is an infrared communication device, a client server device, a cellular communication device, a radio frequency communication device, or an internet based communication device.

25. The drilling rig of claim 14, further comprising a fluid level sensor in communication with the controller for sensing when the drilling fluid rises above a preset limit adjacent the filtration means and for transmitting sensed fluid level values to the controller, wherein the controller further comprises computer instructions in the data storage to prevent the drilling fluid from entering the gas analyzer when the sensed fluid level values exceed the preset limit by shutting an ambient air valve.

26. The drilling rig of claim 14, wherein the client device is simultaneously provided with graphical representations, digital representations, or combinations thereof of historical data, updated real-time measurements, or combinations thereof from the gas analyzer system.

* * * * *